US008133861B2

(12) United States Patent
Cusack et al.

(10) Patent No.: US 8,133,861 B2
(45) Date of Patent: Mar. 13, 2012

(54) SYSTEMIC PURINE ADMINISTRATION: MODULATING AXONAL OUTGROWTH OF CENTRAL NERVOUS SYSTEM NEURONS

(75) Inventors: Noel James Cusack, Hopkinton, MA (US); Mark R. Hurtt, Wallingford, CT (US); Richard M. Thorn, Mendon, MA (US)

(73) Assignee: Alseres Pharmaceuticals, Inc., Hopkinton, MA (US)

( * ) Notice: Subject to any disclaimer, the term of this patent is extended or adjusted under 35 U.S.C. 154(b) by 224 days.

(21) Appl. No.: 12/393,419

(22) Filed: Feb. 26, 2009

(65) Prior Publication Data

US 2009/0221521 A1 Sep. 3, 2009

Related U.S. Application Data

(60) Provisional application No. 61/032,640, filed on Feb. 29, 2008.

(51) Int. Cl.
*A61K 38/18* (2006.01)
*A61K 31/70* (2006.01)

(52) U.S. Cl. ........................................ 514/8.3; 514/45
(58) Field of Classification Search ........................ None
See application file for complete search history.

(56) References Cited

U.S. PATENT DOCUMENTS

| | | | |
|---|---|---|---|
| 4,954,298 A | 9/1990 | Yamamoto et al. | |
| 5,059,594 A | 10/1991 | Sawai et al. | |
| 5,330,767 A | 7/1994 | Yamamoto et al. | |
| 5,407,609 A | 4/1995 | Tice et al. | |
| 5,447,939 A | 9/1995 | Glasky et al. | |
| 5,455,044 A | 10/1995 | Kim et al. | |
| 5,576,018 A | 11/1996 | Kim et al. | |
| 5,603,972 A | 2/1997 | McFarland | |
| 5,654,008 A | 8/1997 | Herbert et al. | |
| 5,851,451 A | 12/1998 | Takechi et al. | |
| 5,902,834 A | 5/1999 | Porrvik | |
| 6,440,455 B1 | 8/2002 | Benowitz | |
| 6,551,612 B2 | 4/2003 | Benowitz | |
| 6,855,688 B2* | 2/2005 | McKerracher | 424/94.5 |
| 6,855,690 B2 | 2/2005 | Benowitz | |
| 6,903,079 B2* | 6/2005 | Jagtap et al. | 514/45 |
| 6,958,324 B2* | 10/2005 | Salzman et al. | 514/45 |
| 6,987,184 B2 | 1/2006 | Sakata et al. | |
| 7,084,159 B2 | 8/2006 | Cao et al. | |
| 7,199,110 B2* | 4/2007 | Borgens et al. | 514/45 |
| 7,442,686 B2* | 10/2008 | Lasko et al. | 514/1.1 |
| 7,792,576 B2* | 9/2010 | Borgens et al. | 607/3 |
| 2003/0040502 A1 | 2/2003 | Salzman et al. | |
| 2003/0149050 A1 | 8/2003 | Jagtap et al. | |
| 2004/0214790 A1 | 10/2004 | Borgens | |
| 2005/0054558 A1 | 3/2005 | Benowitz | |
| 2005/0148624 A1 | 7/2005 | Itoh et al. | |
| 2005/0277614 A1 | 12/2005 | Benowitz | |
| 2006/0122179 A1 | 6/2006 | Zeldis et al. | |
| 2007/0259044 A1 | 11/2007 | Roy et al. | |

FOREIGN PATENT DOCUMENTS

| | | |
|---|---|---|
| WO | WO9404490 A1 | 3/1994 |
| WO | WO9412957 A1 | 6/1994 |
| WO | WO9611642 A1 | 4/1996 |
| WO | WO2005003180 A2 | 1/2005 |

OTHER PUBLICATIONS (R) Fehlings et al., A Phase I/IIa Clinical Trial of a Recombinant Rho Protein Antagonist in Acute Spinal Cord Injury, Journal of Neurotrauma, 28(5), 787-796 (May 2011).*
International Search Report of corresponding PCT application, PCT/US2009/035289, dated May 8, 2009.
Brown et al., "Rac and Rho Hall of Fame: A Decade of Hypertrophic Signaling Hits", Circulation Research, 98:730-742 (2006).
Chang et al., "Activation of Rho-associated coiled-coil protein kinase 1 (ROCK-1) by caspase-3 cleavage plays an essential role in cardiac myocyte apoptosis", Proc. Natl. Acad. Sci. U.S.A., 103(39): 14495-500 (2006).
Lin et al., "Acute Inhibition of Rho-kinase improves cardiac contractile function in streptozocin-diabetic rats", Cardiovase Res. Jul. 1;75(1):51-8. Epub (2007).
Zhang et al., "Targeted deletion of ROCK1 protects the heart against pressure overload by inhibiting reactive fibrosis", FASEB J. 20(7):916-25 (2006).
Nakagawa et al., "The Uptake of purines by rat brain in vivo and in vitro", J. Neurochem. 20:1143-1149 (1973).
Maroney et al., J. Neurosci. (1998) 18:104-11.
Bennett et al., Proc Natl Acad Sci U.S.A. (2001) 98:13681-6.
Carboni et al., J. Pharmacol Exp. Ther. (2004) 310:25-32.
Dancause et al., 2005, J. Neurosci. 25(44) 10167-10179.
Fukuda et al., ILAR Journal 2003, 44(2) 96-104.
Nudo et al., ILAR Journal 2003, 44(2) 161-174.
Wu Ming-mei et al., "Effects of inosine on axonal regeneration of axotomized retinal ganglion cells in adult rats", Neuroscience Letters, vol. 341, No. 1, Apr. 24, 2003, pp. 84-86.
Extended European Search Report of European Application No. 09718155.6 dated Oct. 6, 2011.

* cited by examiner

*Primary Examiner* — Lawrence E Crane
(74) *Attorney, Agent, or Firm* — Rissman Hendricks & Oliverio LLP

(57) ABSTRACT

Methods for modulating the axonal outgrowth of central nervous system neurons are provided by means of internalized purine administration such as by intravenous, intraarterial, subcutaneous, intramuscular, intraperitoneal, and intrapleural administration. The methods are noted for stimulating the axonal outgrowth of central nervous system neurons following an injury (e.g., stroke, traumatic brain injury, cerebral aneurism, spinal cord injury and the like).

2 Claims, 8 Drawing Sheets

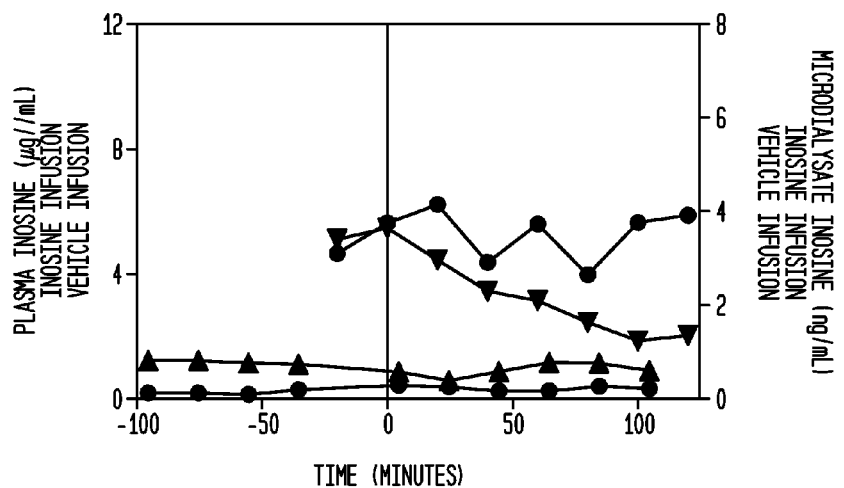
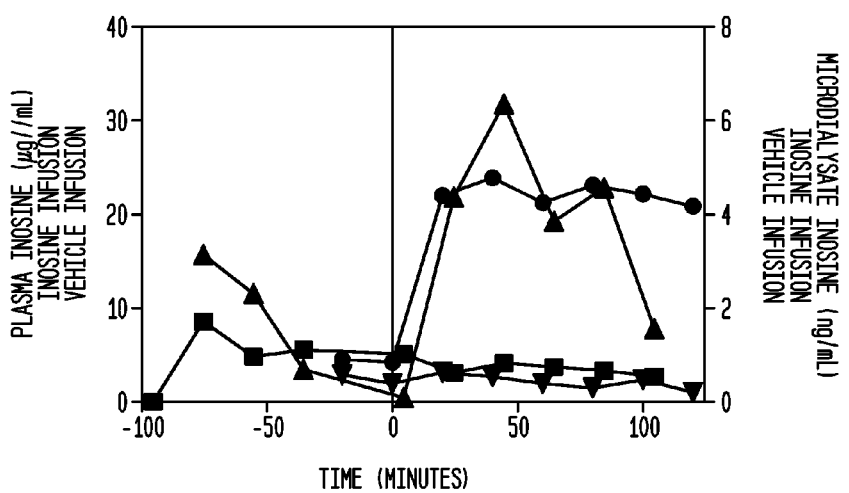

US 8,133,861 B2

SYSTEMIC PURINE ADMINISTRATION: MODULATING AXONAL OUTGROWTH OF CENTRAL NERVOUS SYSTEM NEURONS

RELATED APPLICATIONS

This application claims the benefit of priority under 35 U.S.C. §119(e) of U.S. Provisional Application No. 61/032,640, filed Feb. 29, 2008, the disclosure of which is incorporated herein by reference.

FIELD OF THE INVENTION

The invention relates to methods and compositions for modulating the axonal outgrowth of central nervous system neurons. In particular, the invention provides means of internalized purine administration.

BACKGROUND OF THE INVENTION

After early childhood, injury to the central nervous system (CNS) results in functional impairments that are largely irreversible. Within the brain or spinal cord, damage resulting from stroke, trauma, or other causes can result in life-long losses in cognitive, sensory and motor functions, and even maintenance of vital functions. Nerve cells that are lost are not replaced, and those that are spared are generally unable to re-grow severed connections, although a limited amount of local synaptic reorganization can occur close to the site of injury. Functions that are lost are currently untreatable.

Regenerative failure in the CNS has been attributed to a number of factors, which include the presence of inhibitory molecules on the surface of glial cells that suppress axonal growth; absence of appropriate substrate molecules such as laminin to foster growth and an absence of the appropriate trophic factors needed to activate programs of gene expression required for cell survival and differentiation.

By contrast, within the peripheral nervous system (PNS), injured nerve fibers can re-grow over long distances, with eventual excellent recovery of function. Within the past 15 years, neuroscientists have come to realize that this is not a consequence of intrinsic differences between the nerve cells of the peripheral and central nervous system. Remarkably, neurons of the CNS will extend their axons over great distances if given the opportunity to grow through a grafted segment of PNS (e.g., sciatic nerve). Therefore, neurons of the CNS retain a capacity to grow if given the right signals from the extra-cellular environment. Several factors are believed to contribute to the differing growth potentials of the CNS and PNS. These factors include a partially characterized, growth-inhibiting molecules on the surface of the oligodendrocytes that surround nerve fibers in the CNS, but which is less abundant in the comparable cell population of the PNS (Schwann cells). Also, molecules of the basal laminin and other surfaces that foster growth in the PNS but which are absent in the CNS (e.g., laminin). Others are trophic factors, soluble polypeptides which activate programs of gene expression that underlie cell survival and differentiation. Although such trophic factors are regarded as essential for maintaining the viability and differentiation of nerve cells, the particular ones that are responsible for inducing axonal regeneration in the CNS remain uncertain. Reference is made to U.S. Pat. No. 6,551,612 to Benowitz, the teachings of which are incorporated herein by reference.

Inhibitors of Rho A, siRNA directed against Rho A expression, or Rho may enhance nerve re-growth. *Clostridia botulinum* C3 exotoxin that inhibits Rho A, as do ROCK inhibitors, and siRNA directed against ROCK expression. A recent review article is noted, Brown et al., "Rac and Rho Hall of Fame: A Decade of Hypertrophic Signaling Hits," *Circulation Research*, 98:730-742 (2006).

Further attention is drawn to Chang et al., "Activation of Rho-associated coiled-coil protein kinase 1 (ROCK-1) by caspase-3 cleavage plays an essential role in cardiac myocyte apoptosis," *Proc Natl Acad Sci U S A.*, 103(39):14495-500 (2006); and Lin et al., "Acute Inhibition of Rho-kinase improves cardiac contractile function in streptozocin-diabetic rats," *Cardiovasc Res.* July 1; 75(1):51-8. Epub (2007). Also noted is Zhang, et al., "Targeted deletion of ROCK1 protects the heart against pressure overload by inhibiting reactive fibrosis," FASEB J., 20(7):916-25 (2006).

Notable RhoA antagonists are disclosed in U.S. Pat. No. 6,855,688 to McKerracher, "ADP-ribosyl transferase fusion proteins, pharmaceutical compositions, and methods of use." In this regard, particular mention is made of BA-210, an engineered variant of a naturally occurring bacterial protein known as C3 exoenzyme, corresponding substantially to SEQ. ID NO.: 43 of U.S. Pat. No. 6,855,688 to McKerracher. This is also known as BA-210 and Cethrin.

Previously it was believed that the purines of this invention required intrathecal administration. Reference is made to the administration of [$^{14}$C] radiolabeled inosine given intraperitoneally and the reported [$^{14}$C] inosine in the brain and incorporation in brain RNA NAKAGAWA, S., and GUROFF, G., 1973. The uptake of purines by rat brain in vivo and in vitro. J. Neurochem. 20:1143-1149.

BRIEF DESCRIPTION OF THE DRAWINGS

FIG. 1 presents the data for the plasma and microdialysis inosine concentrations for the 100 mg/kg/hr and 300 mg/kg/hr inosine infusions over time. FIG. 1A through F present plasma inosine in µg/mL and microdialysate inosine in ng/mL.

FIG. 2 presents the data for the plasma and microdialysis inosine concentrations for the 500 mg/kg/hr and 700 mg/kg/hr inosine infusions over time.

FIG. 3 demonstrates that maximal stimulation was observed within 45 minutes for inosine doses of either 500 mg/kg/hr or 700 mg/kg/hr.

SUMMARY OF THE INVENTION

Figure 1A:
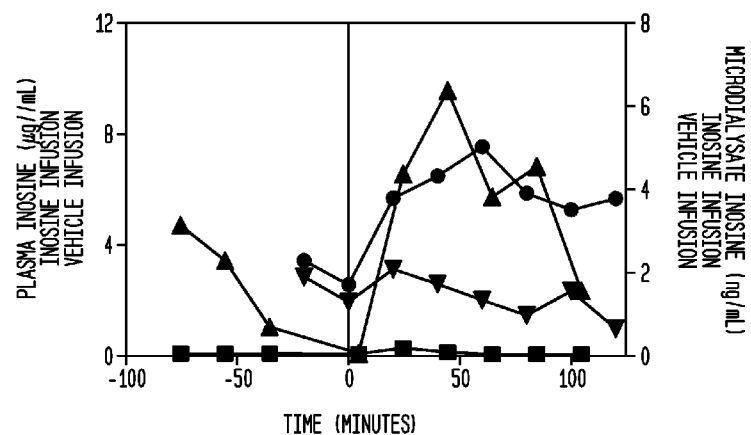
Figure 1B:
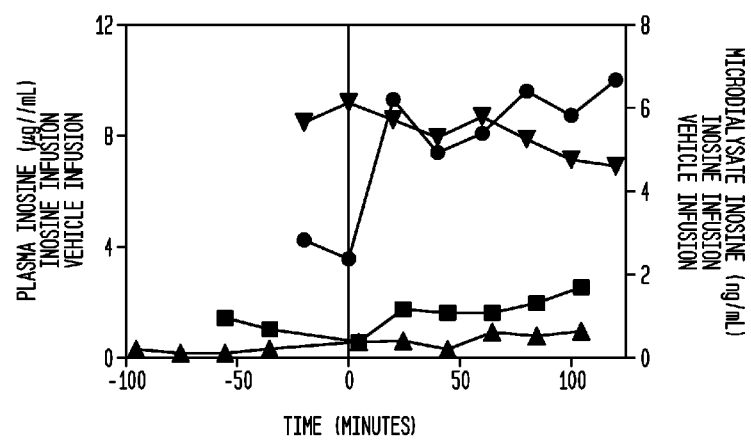
Figure 1E:
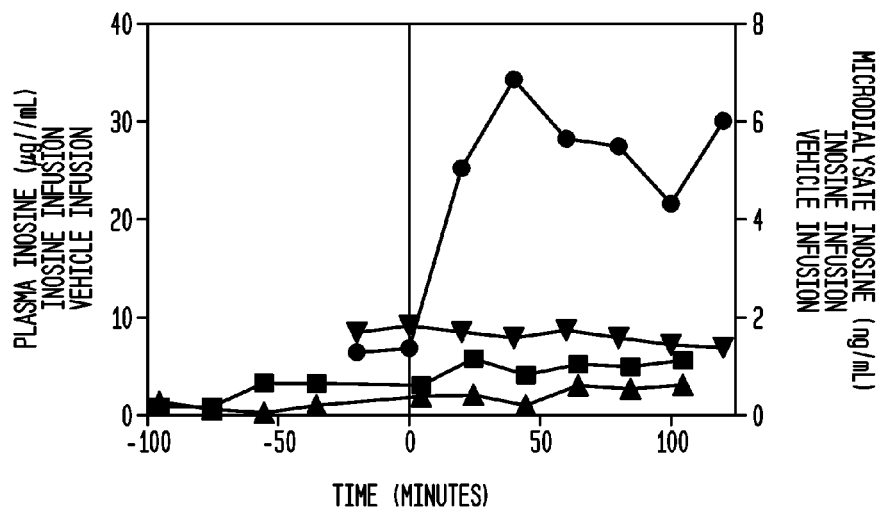
Figure 1F:
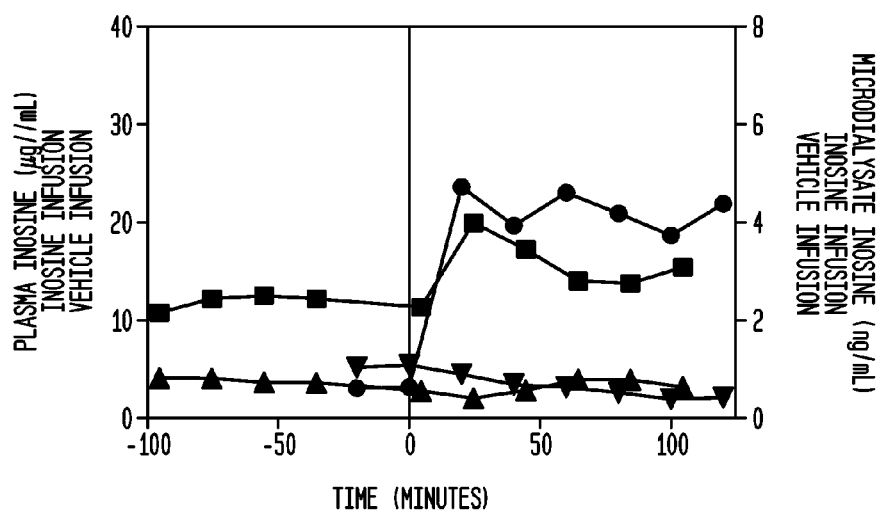
Figure 2A:
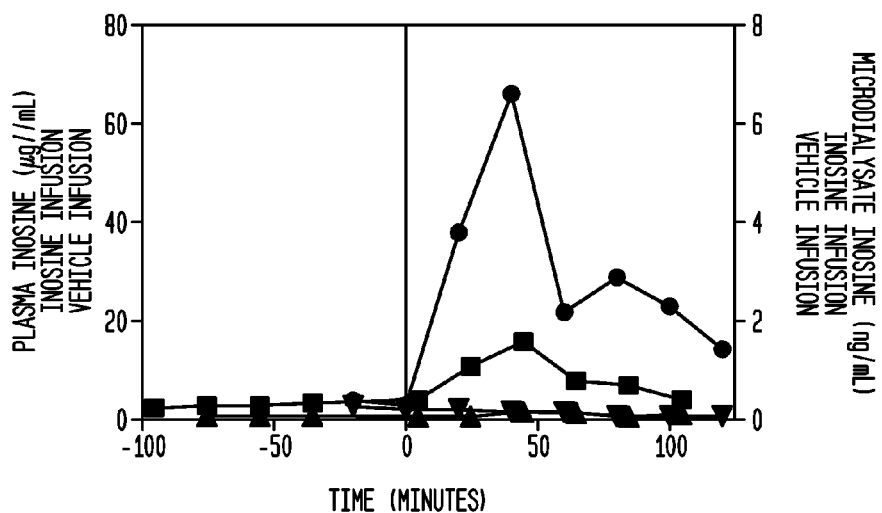
FIG. 2A through F present plasma inosine in µg/mL and microdialysate inosine in ng/mL.
Figure 2B:
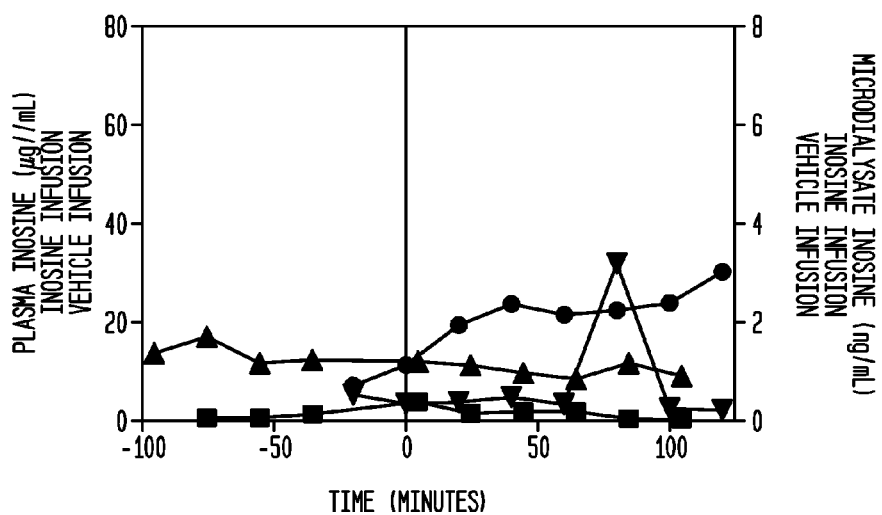
Figure 2C:
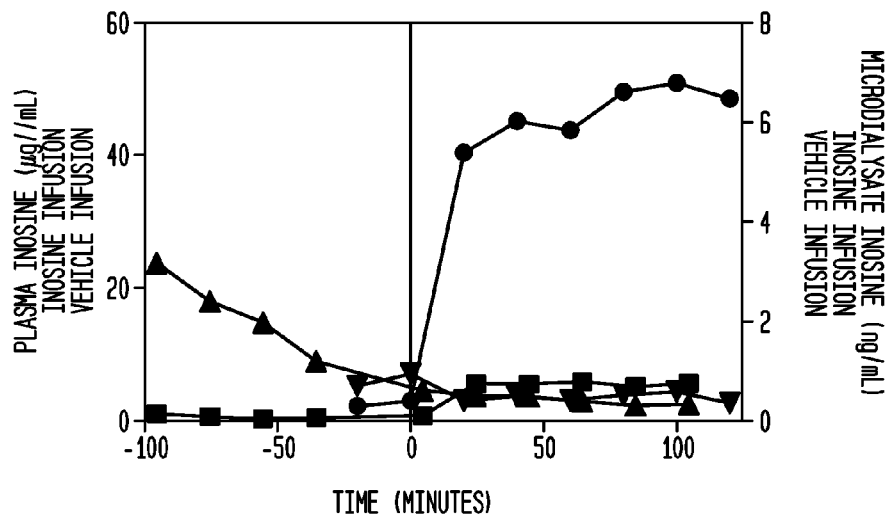
Figure 2D:
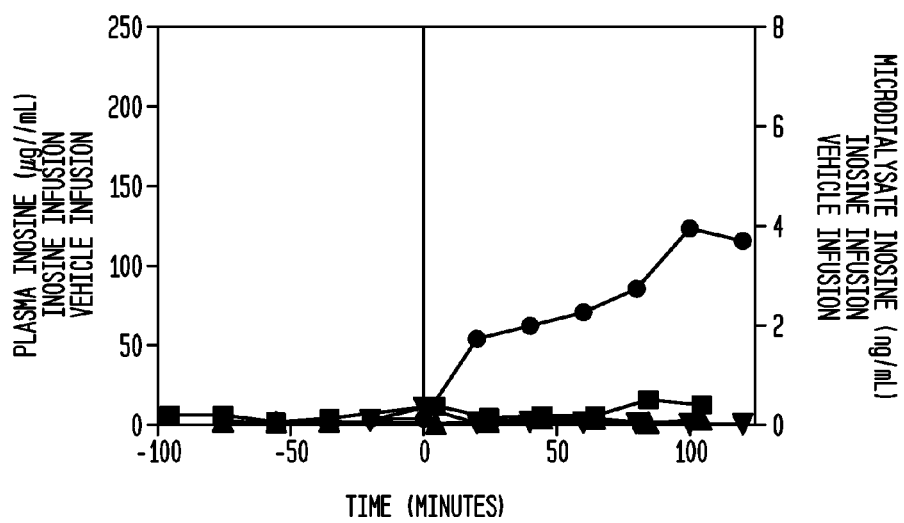
Figure 2E:
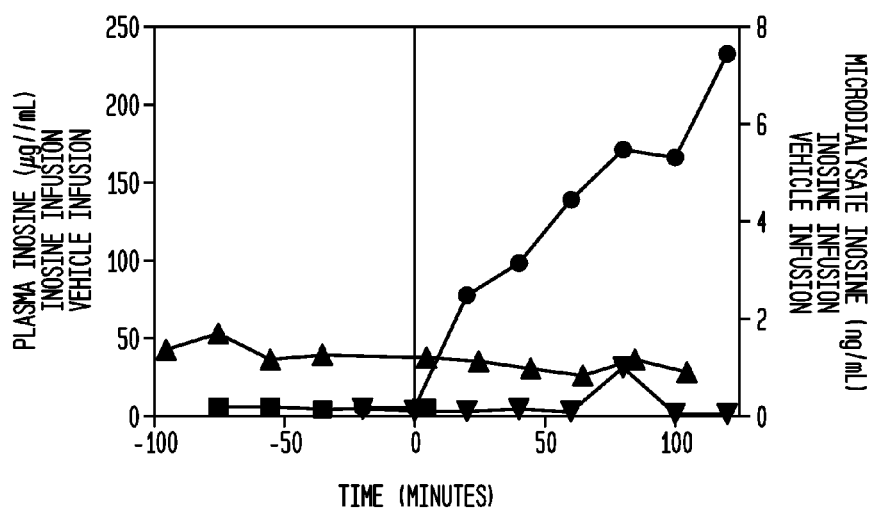
Figure 2F:
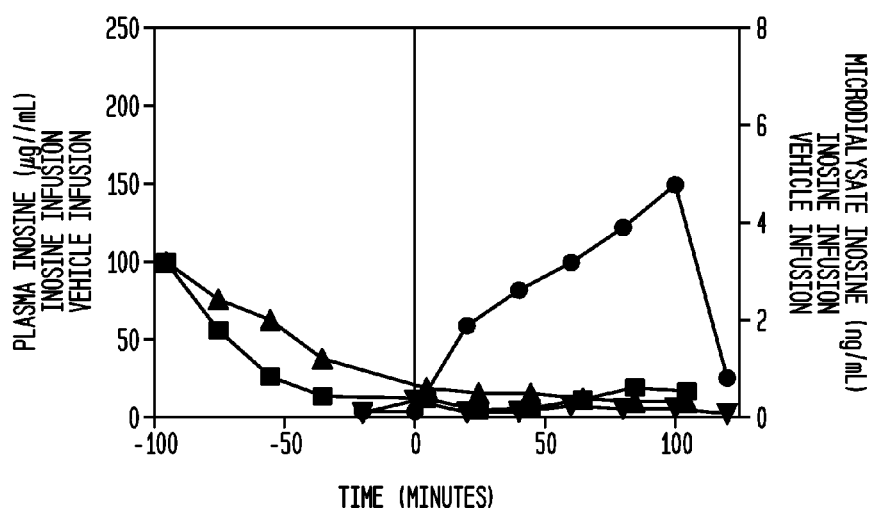

It is discovered that internalized purine administration such as by intravenous, intraarterial, subcutaneous, intramuscular, intraperitoneal, and intrapleural administration is effective in stimulation nerve regrowth in a manner similar to intrathecal purine administration.

One aspect of the invention provides a method for stimulating the axonal outgrowth of central nervous system neurons following spinal cord injury in a mammal, comprising internalized administration of a pharmaceutical composition comprising an effective amount of a purine or purine analog such that axonal outgrowth is stimulated in vivo. Particular note is made of the purine inosine.

Another aspect of the invention provides a pharmaceutical formulation for stimulating the axonal outgrowth of central nervous system neurons following spinal cord injury in a mammal, comprising a pharmaceutically acceptable excipient and a therapeutically effective amount of a purine or purine analog such that axonal outgrowth is stimulated in vivo, wherein the pharmaceutical formulation is suitable for internalized administration.

Further within the contemplated method is addressing central nervous system injury selected from the group consisting of a neuroproliferative disorder, a neuropathic pain syndrome, an injury to retinal ganglion cells, an optic nerve injury, a traumatic brain injury; a stroke related injury, a cerebral aneurysm, and a spinal cord injury In the practice of this method in particular embodiments the therapeutically effective amount of inosine is from about 0.01 mg/kg/day to about 1 g/kg/day, and particularly from about 0.1 g/kg/day to about 0.3 g/kg/day. Further attention is drawn to such method wherein the effective amount of inosine is in the range of from about 0.01 mg/kg/hour to about 200 mg/kg/hour, with particular reference to doses of about 100 mg/kg/hour, 50 mg/kg/hour, 20 mg/kg/hour, 10 mg/kg/hour, 5 mg/kg/hour, 2 mg/kg/hour, 1 mg/kg/hour, and 0.1 mg/kg/hour.

Also, in the practice of this method in particular embodiments the effective amount of inosine is about 1 to about 25 g/day, and particularly about 10 to about 20 g/day. Optionally inosine is administered intravenously, subcutaneously or intraperitoneally.

Particularly noted in the practice of this invention is co-administration of a therapeutically effective dosage of an inhibitor of a kinase selected from the group consisting of JNK, ROCK and RhoA, such as co-administration of a therapeutically effective dosage of cethrin.

A useful formulation of inosine is the pharmaceutical composition comprising from about 0.05 to about 0.2% sodium bicarbonate and about 20 to about 80 mg/mL inosine. Note is made of such formulation wherein the pH is from about 8.9 to about 9.4. In a specific embodiment the composition is about 0.1% sodium bicarbonate and about 70 mg/mL inosine.

DETAILED DESCRIPTION OF THE INVENTION

The present invention provides methods for modulating the axonal outgrowth of central nervous system neurons. The invention is based, at least in part, on the discovery that purine nucleosides (e.g., inosine and guanosine) and analogs thereof, induce stimulation of axonal outgrowth from both goldfish as well as mammalian retinal ganglion cells (see, e.g., U.S. Pat. No. 6,551,612 and U.S. Pat. No. 6,440,455 and US Application Publication No. 2005/0277614, the teachings of which are incorporated herein by reference in their entirety).

It has now been discovered that axonal outgrowth of CNS neurons, may be modified using administration of purine nucleoside or analog thereof beyond the intrathecal mode for contacting the central nervous system neurons.

Applicants have discovered that it is useful to employ internalized purine administration such as by intravenous, intraarterial, subcutaneous, intramuscular, intraperitoneal, and intrapleural administration to modulate axonal outgrowth In the interest of clarity, the following definitions are provided:

A. "Modulating" in relation to modulating the axonal outgrowth of central nervous system neurons is used expansively to include the capacity to stimulate or inhibit axonal outgrowth of central nervous system neurons to achieve some amount of reenervation, in the treatment of targeted CNS injury.

B. "Outgrowth" shall mean the process by which axons grow out of a CNS neuron. The outgrowth can result in a totally new axon or the repair of a partially damaged axon. Outgrowth is typically evidenced by extension of an axonal process of at least about five cell diameters in length measured at the cell body.

C. "CNS neurons" shall be understood expansively to include the neurons of the brain and the spinal cord which are unresponsive to nerve growth factor (NGF). The term is not intended to include support or protection cells such as astrocytes, oligodentrocytes, microglia, ependyma and the like, nor is it intended to include peripheral nervous system (e.g., somatic, autonomic, sympathetic or parasympathetic nervous system) neurons. Attention is drawn to mammalian CNS neurons such as human neurons.

D. "Contacting" is intended to include in vivo internalized purine administration such as by intravenous, intraarterial, subcutaneous, intramuscular, intraperitoneal, and intrapleural administration bringing a purine nucleoside or analog thereof into proximity with a CNS neuron, such that the purine nucleoside or analog thereof can modulate the outgrowth of axonal processes from said CNS neuron. In some embodiments such internalized administration is by way of a shunt.

E. "Purine nucleoside" shall mean any purine base linked to a sugar, or an analog, derivative or prodrug thereof. For example, purine nucleosides include, but are not limited to, guanosine, inosine or adenosine and analogs including 6-thioguanosine (6-TG) and the like.

Examples of purine nucleosides include, but are not limited to: 9-(2'-deoxy-2'-fluoro-beta-D-ribofuranosyl)adenine, 9-(2'-deoxy-2'-fluoro-beta-D-arabinofuranosyl)adenine, 9-(2'-azido-2'-deoxy-beta-D-ribofuranosyl)adenine (2'-N3-riboA), 9-(2-azido-2'-deoxy-beta-D-arabinofuranosyl)adenine, Pentostatin, and Tubercidin.

Examples of purine nucleosides are described in WO 01/77075, WO 02/076400, WO 01/52860, WO 2005/117910, WO 2006/034190, US 2003/0040502, US 2003/0149050, US 2005/0282768, US 2006/0128652, U.S. Pat. No. 6,958,324, and U.S. Pat. No. 6,903,079, each of which are incorporated herein by reference in their entirety. Examples of inosine derivatives are described in US 2006/094870, US 2003/204080, US 2003/004330, U.S. Pat. No. 6,500,946, and U.S. Pat. No. 3,337,528.

F. "Internalized" with reference to purine administration shall mean by systemic and parenteral administration wherein the purine reaches the area in need of treatment. In one embodiment, internalized administration is parenteral administration. Examples of internalized administration include, but are not limited to, intravenous, intraarterial, subcutaneous, intramuscular, intraperitoneal, and intrapleural administration. Internalized administration optionally includes administration by way of a shunt. Internalized administration optionally includes transdermal, intraocular and iontophoresis administration. Internalized administration optionally includes local bolus or infusion during surgery or topical application, (e.g., directly to a wound or in conjunction with a wound dressing), by injection, by means of a catheter. Intravenous administration alternatively comprises administration by bolus or infusion. In one embodiment, internalized administration is contrasted with intrathecal and oral administration.

G. "Subject" shall mean animals susceptible to CNS injuries, including mammals, with specific reference to primates including humans. Noted too are dogs, cats, horses and cattle.

H. "Injury" shall mean damage, insult, or trauma which directly or indirectly affects the functioning of the CNS. Examples of such injuries include, but are not limited to, a neuroproliferative disorder, a neuropathic pain syndrome, an injury to retinal ganglion cells; an optic nerve injury, a traumatic brain injury; a stroke related injury; a cerebral aneurysm, and a spinal cord injury. Spinal cord injury includes, but is not limited to, monoplegia, diplegia, paraplegia, hemiplegia and quadriplegia.

I. "Stroke" shall mean an illness caused by a blood clot or bleeding in the brain. Stroke indicia include sudden diminution or loss of consciousness, sensation, and voluntary motion. Stroke often stems from rupture or obstruction of a cranial artery.

J. "Traumatic brain injury" also called acquired brain injury or simply head injury, is a condition occurring when a sudden trauma causes damage to the brain. Traumatic brain injury is often associated blow to the head, not necessarily penetrating the skull. Usually, the initial trauma can result in expanding hematoma, subarachnoid hemorrhage, cerebral edema, raised intracranial pressure (ICP), and cerebral hypoxia, which can, in turn, lead to severe secondary events due to low cerebral blood flow (CBF).

K. "Polymer" or "Polymeric" shall include a molecular structural framework comprised of repeating monomer units which is capable of internalized delivery of therapeutic amount of a purine nucleoside or analog thereof. The terms are used expansively to include co-polymers and homopolymers e.g., synthetic or naturally occurring. Linear polymers, branched polymers, block polymers and cross-linked polymers are also meant to be included.

For example, polymeric materials suitable for forming the pharmaceutically acceptable formulation employed in the present invention, include naturally derived polymers such as albumin, alginate, cellulose derivatives, collagen, fibrin, gelatin, and polysaccharides, as well as synthetic polymers such as polyesters (PLA, PLGA), polyethylene glycol, poloxomers, polyanhydrides, and pluronics. These polymers are biocompatible with the nervous system, including the central nervous system, they are biodegradable within the central nervous system without producing any toxic byproducts of degradation, and they possess the ability to modify the manner and duration of purine nucleoside release by manipulating the polymer's kinetic characteristics.

L. "Biodegradable" as to a polymer shall mean that the polymer will degrade over time by the action of enzymes, by hydrolytic action and/or by other similar mechanisms in the body of the subject.

M. "Biocompatible" as to a polymer shall mean that the polymer is compatible with a living tissue or a living organism by not being toxic or injurious and by not causing an immunological rejection.

A number of inosine formulations were examined. Preparatory steps were as follows:

Preparation of Solutions
  a. Preparation of Phosphate Buffered Saline
    Combine 4 g NaCl, 100 mg KCl, 720 mg $Na_2HPO_4$, and 120 mg $KH_2PO_4$ with 500 mL of distilled water. Mix well.
  b. Preparation of Normal Saline
    Add 4.5 g of NaCl to a 500 mL volumetric flask. Dissolve all solids completely and bring to volume with distilled water. Mix well.
  c. Preparation of 5% Dextrose Solution
    Add 25 g of Dextrose to a 500 mL volumetric flask. Dissolve all solids completely and bring to volume with distilled water. Mix well.
  d. Preparation of 50 mM TRIS Base Buffer
    Combine 1.514 mg of TRIS base with about 200 mL of distilled water and adjust to pH 9 with 6N HCl. Bring volume to 250 mL with water. Mix well.
  e. Preparation of 10% (v/v) Polyethylene Glycol-400
    Combine 18 mg of SDS with 100 mL of distilled water. Mix well.
  f. Preparation of 0.18% Sodium Dodecyl Sulfate
    Combine 18 mg of SDS with 100 mL of distilled water. Mix well.
  g. Preparation of 15%, 10% and 5% Meglumine
    Combine 150 g of meglumine with 1 L of distilled water. Mix well. Dilute by factors of ⅔ or ⅓ with distilled water to prepare 10% and 5% meglumine.
  h. Preparation of 1.5% Sodium Carbonate
    Combine 1.5 mg. Na2CO3 with 100 mL of distilled water. Mix well.
  i. Preparation of 4.2%, 1.5%, 0.5%, 0.25%, and 0.1% Sodium Bicarbonate
    Combine 4.2 g, 1.5 g or 100 mg of NaCO3 with 100 mL of distilled water to produce 4.2 g, 1.5 g or 100 mg of NaCO3 with 100 mL of distilled water to produce 4.2%, 1.5%, and 0.5% NaCO3 respectively. Dilute the 1.5% NaCO3 by ⅓ or ⅙ to produce 0.5% and 0.25% NaCO3 respectively. Mix well.

General Preparation

Inosine protype formulations were prepared by adding inosine drug substance to tare vials containing about 3-5 mL of aqueous solutions containing various pharmaceutical excipients in various concentrations. It is noted that inosine solubility was much higher in entirely aqueous solutions. Common I.V. solutions such as phosphate buffered saline, normal saline and 5% dextrose in water are noted. It was discovered that inosine solubility was greatly enhanced in high pH environments.

Multiple formulations were prepared using meglumine (formulations 16-45). Megulmine is known to function both as a solubilizing and alkalizing agent, thus precluding the need for a buffering species which would unfavorably increase ionic strength in the formulation. Particular note is made of formulation using sodium bicarbonate, despite the lower inosine solubility in these solutions, with specific emphasis on formulation 80, which contained 0.1% sodium bicarbonate 70 mg/mL inosine, pH 9.2. This solution is 261 mM. It was determined that a significant parameter for increasing inosine solubility was the pH of the solution. Also higher concentrations of saline solutions reduced solubility. It is noted that a formulation of 0.1% sodium bicarbonate as an inosine compatible buffer with an alkaline pKa to facilitate GRAS obtaining (Generally Regarded as Safe) regulatory standing. Formulation 80 (70 mg/mL) was diluted to 50 mg/mL and administered intravenously to rats and the intracranial inosine level measured. Dosages of about 800 to 1000 mg of inosine per kg body weight as administered i.v. over about two hours appeared to saturate the vascular uptake mechanism yielding a significant rise in inosine plasma levels. increased interstitial inosine approximately 500% as compared with the baseline/predose concentrations. Dosages of 160-200 mg/kg/2 hrs and 480-600 mg/kg/2 hrs increased inosine levels approximately 170% above background. The vehicle dose produced mild increases in brain inosine levels (150% of baseline). Formulation 80 (70 mg/mL) at doses of 1120-1400 mg/kg/2 hrs of inosine per kg body weight did not increased interstitial inosine above the vehicle dose. The last value suggests a biphasic dose response.

The composition of each formulation is provided in Table I. The pH of the formulation is reported for those formulations for which it was tested.

TABLE I

Formulations

| Formulation Number | Formulation Components | Approx. Potency | Comments |
|---|---|---|---|
| 1 | Phosphate Buffered Saline | 20 mg/mL | Saturated |
| 2 | Normal Saline | 5 mg/mL | Saturated |
| 3 | 5% Dextrose | 33 mg/mL | Saturated |
| 4 | 10% Polyethylene Glycol | 15 mg/mL | Saturated |
| 5 | 50 mM Bicarbonate Buffer, pH 8 | 20 mg/mL | Saturated |
| 6 | 50 mM TRIS Base, pH 8 | 26 mg/ML | Saturated |
| 7 | 0.018% (w/v) SDS | 15 mg/mL | Saturated |
| 8 | 50 mM TRIS Base, not pH adjusted | Not Recorded | Observed pH change with Inosine saturation |
| 9 | 125 mM TRIS Base, not pH adjusted | 43 mg/mL | Saturated |
| 10 | 100 mM Diethanolamine, pH 9 | 78 mg/ML | Saturated |
| 11 | 250 mM Diethanolamine, pH 9.3 | 100 mg/mL | Saturated |
| 12 | 0.018% (w/v) SDS, 250 mM Diethanolamine | NA | SDS degraded by base |
| 13 | 20 mM Diethanolamine, pH 9 | 100 mg/ML | Saturated |
| 14 | 50 mM Bicarbonate Buffer, pH 9.5 | 120 mg/mL | Saturated |
| 15 | 50 mM Bicarbonate Buffer, pH 9.5 | 120 mg/mL | Repeat of form #14, using Spectrum lot of Inosine |
| 16 | 5% Meglumine, pH 9 | 140 mg/mL | Saturated |
| 17 | 10% Meglumine, pH 9 | 115 mg/mL | Saturated |
| 18 | 15% Meglumine, pH 9.71 | 130 mg/mL | Soluble; used to investigate pH adjustments |
| 19 | 15% Meglumine, pH 9.66 | 131 mg/mL | Soluble; used to investigate pH adjustments |
| 20 | 15% Meglumine, pH 9.51 | 130 mg/mL | Soluble; used to investigate pH adjustments |
| 21 | 15% Meglumine, pH 9.17 | 133 mg/mL | Soluble; used to investigate pH adjustments |
| 22 | 15% Meglumine, pH 8.64 | 133 mg/mL | Soluble; used to investigate pH adjustments |
| 23 | 15% Meglumine, pH 8.67 | 148 mg/mL | Soluble; used to investigate pH adjustments |
| 26 | 7.5% Meglumine, pH 9.0 | 137 mg/mL | Saturated |
| 27 | 10% Meglumine, pH 9.3 | 129 mg/mL | Soluble |
| 28 | 15% Meglumine, pH 9.0 | 130 mg/mL | Soluble |
| 29 | 10% Meglumine, pH 7.1 | 129 mg/mL | Ppt. formed upon pH adjustment |
| 30 | 10% Meglumine, pH 8.9 | 129 mg/mL | Soluble |
| 31 | 15% Meglumine, pH 8.5 | 130 mg/mL | Ppt. after 5 days at 2-8° C. |
| 32 | 10% Meglumine, pH 8.4 | 129 mg/mL | Ppt. after 3 hours at 2-8° C. |
| 33 | 15% Meglumine, pH 8.0 | 130 mg/mL | Ppt. after 3 hours at 2-8° C. |
| 34 | 10% Meglumine, pH 7.4 | 129 mg/mL | Ppt. formed upon pH adjustment |
| 35 | 15% Meglumine, pH 8.5 | 155 mg/mL | Ppt. after overnight storage at 2-8° C. |
| 36 | 15% Meglumine, pH 9.0 | 150 mg/mL | Soluble at 2-8° C. |
| 37 | 5% Meglumine, pH 12.0 | 131 mg/mL | Saturated |
| 38 | 5% Meglumine, pH 9.0 | 131 mg/mL | Add prepared solvent to inosine; saturated |
| 39 | 5% Meglumine, pH 9.0 | 131 mg/mL | Add water to inosine/meglumine; Saturated |
| 40 | 5% Meglumine, pH 9.0 | 131 mg/mL | Start at high pH, adjust down w/HCl; soluble |
| 41 | 5% Meglumine, pH 9.0 | 130 mg/mL | Use less NaOH require less HCl; soluble |
| 42 | 5% Meglumine, pH 9.0 | 130 mg/mL | Use less NaOH require less HCl; soluble |
| 43 | 5% Meglumine, pH 9.0 | 154 mg/mL | Repeat form 42 w/more inosine; saturated |
| 44 | 9.5% Meglumine, pH 9.0 | 144 mg/mL | Assess ruggedness of form 30; ppt after 5 days |
| 45 | 4.7% Meglumine, pH 9.0 | 144 mg/mL | Assess ruggedness of form 40; saturated |
| 46 | 0.3% Diethanolamine pH 8.9 | 100 mg/mL | Solubilize at pH 12.8 stayed in to pH 8.9 |
| 47 | 0.3% Diethanolamine pH 9.8 | 100 mg/mL | Added NaOH first; saturated |
| 48 | 0.3% Diethanolamine pH 8.9 | 80 mg/mL | Solubilize at pH 11.8 stayed in to pH 8.7, ppt. after 4 days |
| 49 | 1.5% Sodium Carbonate pH 8.8 | 100 mg/mL | Saturated |
| 50 | 1.5% Sodium Carbonate pH 11.5 | 100 mg/mL | Saturated |
| 51 | 1.5% Sodium Carbonate pH 8.9 | 80 mg/mL | Soluble |
| 52 | 1.5% Sodium Bicarbonate pH 8.9 | 100 mg/mL | Saturated |
| 53 | 1.5% Sodium Bicarbonate pH 8.9 | 80 mg/mL | Saturated |

TABLE I-continued

Formulations

| Formulation Number | Formulation Components | Approx. Potency | Comments |
|---|---|---|---|
| 54 | 1.5% Sodium Bicarbonate pH 9.0 | 80 mg/mL | Soluble at pH 9.7, ppt. formed at 2-8° C. after pH adjustment |
| 55 | 1.5% Sodium Bicarbonate pH 9.0 | 100 mg/mL | Attempted to solubilize at high pH, saturated |
| 56 | 1.5% Sodium Bicarbonate pH 9.0 | 80 mg/mL | Ppt. formed after 1 hour at 2-8° C. |
| 57 | 4.2% Sodium Bicarbonate | 115 mg/mL | Saturated |
| 58 | 4.2% Sodium Bicarbonate pH 9.5 | 100 mg/mL | Ppt. formed after 5 minutes at room temp |
| 59 | 4.2% Sodium Bicarbonate pH 9.6 | 110 mg/mL | Saturated |
| 60 | 4.2% Sodium Bicarbonate pH 9.0 | 80 mg/mL | Soluble at pH 9.3, ppt. formed ater pH adjustment |
| 61 | 1.5% Sodium Bicarbonate pH 8.9 | 80 mg/mL | Soluble at pH 9.8, ppt. formed at 2-8° C. after pH adjustment |
| 62 | 1.5% Sodium Bicarbonate pH 9.0 | 134 mg/mL | Soluble at pH 9.2, ppt. formed at 2-8° C. after pH adjustment |
| 63 | 0.5% Sodium Bicarbonate pH 9.0 | 130 mg/mL | Soluble at pH 9.2, ppt. formed at 2-8° C. after pH adjustment |
| 64 | 0.5% Sodium Bicarbonate pH 8.9 | 93 mg/mL | Saturated |
| 65 | 0.5% Sodium Bicarbonate pH 9.1 | 134 mg/mL | Saturated |
| 66 | 0.5% Sodium Bicarbonate pH 9.0 | 120 mg/mL | Saturated |
| 67 | 0.5% Sodium Bicarbonate pH 9.1 | 110 mg/mL | Ppt. formed after 5 days at 2-8° C. |
| 68 | 0.25% Sodium Bicarbonate pH 9.1 | 120 mg/mL | Ppt. formed after 5 days at 2-8° C. |
| 69 | 0.25% Sodium Bicarbonate pH 9.2 | 134 mg/mL | Ppt. formed after 1 hour at room temp |
| 70 | 0.1% Sodium Bicarbonate pH 9.1 | 134 mg/mL | Ppt. formed after 1 hour at room temp |
| 71 | 0.1% Sodium Bicarbonate pH 9.3 | 134 mg/mL | Saturated |
| 72 | 0.1% Sodium Bicarbonate pH 9.2 | 134 mg/mL | Saturated |
| 73 | 0.1% Sodium Bicarbonate pH 9.1 | 134 mg/mL | Ppt. formed after 1 hour at 2-8° C. |
| 74 | 0.1% Sodium Bicarbonate pH 9.1 | 120 mg/mL | Saturated |
| 75 | 0.1% Sodium Bicarbonate pH 9.1 | 120 mg/mL | Ppt. formed after 1 hour at room temp |
| 76 | 0.1% Sodium Bicarbonate pH 9.2 | 110 mg/mL | Ppt. formed after 12 hours at room temp |
| 77 | 0.1% Sodium Bicarbonate pH 9.5 | 110 mg/mL | Saturated |
| 78 | 0.1% Sodium Bicarbonate pH 10.2 | 134 mg/mL | Saturated |
| 79 | 0.1% Sodium Bicarbonate pH 9.4 | 80 mg/mL | Ppt. formed after 1 hour at room temp |
| 80 | 0.1% Sodium Bicarbonate pH 9.2 | 70 mg/mL | Soluble; selected formulation |

Formulation Process

Formulation 80 which contained 0.1% sodium bicarbonate and 70 mg/mL inosine, pH 9.2 is particularly noted. It is believed to have adequate tolerability of sodium bicarbonate pH 9.2 and a useful potency of 70 mg/mL, and observed initial physical stability of the formulation.

A. GLP Formulating Procedure

The following procedure was developed and executed for the production of a batch of the inosine formulation. Ethanol rinsed gloves were worn when preparing the formulation. An area in a high-potency hood was prepared by rinsing all contact surfaces with Isopropyl Alcohol. All containers (one 20 mL glass scintillation vial and eight 2 mL glass parenteral vials with silicone stoppers) were triple rinsed with Ethanol. The containers were placed on a drying rack and allowed to sit until all Ethanol had evaporated. Each scintillation vial was tared on an analytical balance and 10 mg of sodium bicarbonate followed by 0.7 g of inosine were added. All solids were dissolved with 10 mL of $H_2O$, with mixing on a Vortex Genie as needed. A small aliquot was removed to verify the pH and if needed, adjust the pH to 9.2 using 6N HCl or 10N NaOH. The formulation was transferred to a 10 mL syringe equipped with a 0.2 um nylon syringe tip filter, discarding about 1 mL of filtrate. The remaining formulation was filtered in 1 mL increments into glass parenteral vials and stoppers were immediately placed firmly into the vials. After all vials had been filled and stoppered, each vial was crimped closed using an aluminum parenteral vial flip-off seal.

B. Inosine Formulation Batch

During the batch preparation of the inosine formulation, the actual weight of inosine used was 704.1 mg, and that of sodium bicarbonate was 10.3 mg. The formulation required approximately two minutes of vortex mixing in order to go into solution. The pH of the filtered formulation was 9.23.

In some embodiments polymers can be prepared using methods known in the art (Sandler, S. R.; Karo, W. Polymer Syntheses; Harcourt Brace: Boston, 1994; Shalaby, W.; Ikada, Y.; Langer, R.; Williams, J. *Polymers of Biological and Biomedical Significance* (ACS Symposium Series 540: American Chemical Society: Washington, D.C., 1994). Polymers can be designed to be flexible. In some instances flexibility is determined by the distance between the bioactive side-chains and the length of a linker between the polymer backbone and the group being controlled. Other suitable polymers and methods for their preparation are, without limitation, described in U.S. Pat. Nos. 5,455,044 and 5,576,018, the contents of which are incorporated herein by reference.

In some instances polymeric formulations are formed by dispersion of the purine nucleoside within liquefied polymer, as described in U.S. Pat. No. 4,883,666, the teachings of which are incorporated herein by reference or by such methods as bulk polymerization, interfacial polymerization, solution polymerization and ring polymerization as described in Odian G., *Principles of Polymerization and ring opening polymerization,* 2nd ed., John Wiley & Sons, New York, 1981, the contents of which are incorporated herein by reference. The properties and characteristics of the formulations are controlled by varying such parameters as the reaction temperature, concentrations of polymer and purine nucleoside, types of solvent used, and reaction times.

The pharmacokinetic profile of inosine has been studied following oral administration of inosine Pranobex, which is used in Europe to treat infections such as Herpes simplex, influenza, zoster and type B viral hepatitis, (Campoli-Richards, D M, et al. (1986) *Drugs,* 32; 383-424). Inosine Pranobex has also been studied for the long term modification of mammalian neural activity (See Glasky, U.S. Pat. No. 5,447, 939)

The pharmaceutical compositions containing one or more active agents may be formulated according to conventional pharmaceutical practice (see, for example, *Remington. The Science and Practice of Pharmacy*, (20th ed.) ed. A. R. Gennaro, 2000, Lippincott Williams & Wilkins, Philadelphia, Pa. and *Encyclopedia of Pharmaceutical Technology*, eds., J. Swarbrick and J. C. Boylan, 1988-2002, Marcel Dekker, New York), the contents of which are incorporated herein by reference in their entirety.

The compositions of the present invention are, in one aspect, administered parenterally or systemically. Examples of parenteral administration include but are not limited to intramuscular, intraperitoneal, intravenous, ocular, or subcutaneous administration.

Ocular administration may be topical, by injection or by implant. Examples of ocular administration include, but are not limited to, intraocular, periocular, retro-bulbar, intravitreal, subconjunctival, subtenon, back of the orbit, administration. Topical ocular application may be as an ointment, gel, mist, or eye drops.

Formulations for parenteral or systemic administration include sterile aqueous or non-aqueous solutions, suspensions, or emulsions. A variety of aqueous carriers can be used, e.g., water, buffered water, saline, and the like. Non-limiting examples of other suitable vehicles include DMSO, polypropylene glycol, polyethylene glycol, vegetable oils, gelatin, hydrogels, hydrogenated naphthalenes, and injectable organic esters, such as ethyl oleate. Such formulations may also contain auxiliary substances, such as preserving, wetting, buffering, emulsifying, and/or dispersing agents. Biocompatible, biodegradable lactide polymer, lactide/glycolide copolymer, or polyoxyethylene-polyoxypropylene copolymers may be used to control the release of the active ingredients.

In one embodiment, the outgrowth of CNS neurons is stimulated, such as by internalized administration of inosine or guanosine nucleosides or analogs thereof. In another embodiment, the outgrowth of CNS neurons is inhibited, using a 6-thioguanine (6-TG) or 6-thioguanine nucleoside via internalized administration.

The invention also provides methods for stimulating the outgrowth of central nervous system neurons following an injury. The method involves internalized administration of a purine nucleoside (e.g., inosine or guanosine) or analog, derivative, polymorph, stereoisomer or prodrug thereof to a subject in need of such treatment.

In one embodiment the compositions and methods of the present invention are useful in treating an ocular neuron disorder. "Ocular neuron disorders" include, but are not limited to, retina or optic nerve optic nerve disorders, optic nerve damage and optic neuropathies, disorders of the optic nerve or visual pathways, toxic amblyopia, optic atrophy, higher visual pathway lesions, disorders of ocular motility, third cranial nerve palsies, fourth cranial nerve palsies, sixth cranial nerve palsies, internuclear ophthalmoplegia, gaze palsies, and free radical induced eye disorders.

Optic neuropathies include, but are not limited to, ischemic optic neuropathy, inflammation of the optic nerve, bacterial infection of the optic nerve, optic neuritis, optic neuropathy, and papilledema (choked disk), papillitis (optic neuritis), retrobulbar neuritis, optic neuritis (ON), anterior ischemic optic neuropathy (AION), commotio retinae, glaucoma, macular degeneration, retinitis pigmentosa, retinal detachment, retinal tears or holes, diabetic retinopathy and iatrogenic retinopathy.

One particular ocular neuron disorder is glaucoma. Types of glaucoma include, but are not limited to, primary glaucoma, chronic open-angle glaucoma, acute or chronic angleclosure, congenital (infantile) glaucoma, secondary glaucoma, and absolute glaucoma.

In other embodiments, the ocular neuron disorder to be treated includes, but is not limited to, normotensive excavatory optic neuropathy, ischemic optic neuropathy, toxic optic neuropathy, traumatic optic neuropathy, or idiopathic optic neuropathy.

Examples of normotensive excavatory optic neuropathy include primary optic atrophy, ocular ischemic syndrome, shock-associated optic atrophy or chronic systemic hypotension. Examples of ischemic optic neuropathy include anterior ischemic optic neuropathy, posterior ischemic optic neuropathy, giant cell arteritis, or Foster-Kennedy syndrome. Examples of toxic optic neuropathy include drug induced optic neuropathy or nutritional optic neuropathy. Examples of traumatic optic neuropathy include inflammatory optic neuropathy or neuroretinitis. Examples of idiopathic optic neuropathy include optic nerve drusen or benign intracranial hypertension. In certain aspects of the present invention, multiple optical nerve diseases occurring in the same patient are treated using the compositions and methods of the invention.

Pharmaceutically Acceptable Formulations

In the method of the invention, the purine nucleoside or analog thereof can be internalized by administration of a pharmaceutically acceptable formulation. The present invention pertains to any pharmaceutically acceptable formulations.

Particular note is made of pharmaceutically acceptable formulations having concentrations of inosine of about 70 mg/mL or more.

Other examples of pharmaceutically acceptable formulations, include but are not limited to, synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

In one embodiment, the pharmaceutically acceptable formulations comprise a polymeric matrix.

In addition to the purine nucleoside, the pharmaceutically acceptable formulation used in the method of the invention optionally comprise additional pharmaceutically acceptable carriers and/or excipients. As used herein, "pharmaceutically acceptable carrier" includes any and all solvents, dispersion media, coatings, antibacterial and anti fungal agents, isotonic and absorption delaying agents, and the like that are physiologically compatible. Excipients optionally include pharmaceutically acceptable stabilizers and disintegrants.

Examples of suitable excipients, include but are not limited to, those described in: *Handbook of Pharmaceutical Excipi-*

*ents*, A. Wade, Paul J. Sheskey and P. Weller 2003, Pharmaceutical Press, London, which is incorporated herein by reference in its entirety. Examples of suitable excipients for use in injectable products, include but are not limited to, those described in: *Excipients and their use in Injectable Products*, A. Nema et al. *PDA Journal of Pharmaceutical Science & technology*, 1997, 51(4), 166-171, which is incorporated herein by reference in its entirety.

In one embodiment, the pharmaceutical composition comprises sodium chloride (NaCl). In another embodiment, the pharmaceutical composition comprises 0.15M NaCl.

The pharmaceutical composition optionally comprises an appropriate buffer system in combination with appropriate excipients that provide the desired osmolality and/or tonicity. Examples of buffer systems include, but are not limited, to sodium phosphate, sodium acetate or sodium borate and sodium bicarbonate buffer systems.

In one embodiment, the pharmaceutical composition comprises phosphate buffered saline (PBS). In another embodiment, the pharmaceutical composition comprises 0.15M NaCl and 20 mM sodium phosphate.

In one embodiment, the pharmaceutical composition comprises sodium acetate (NaAc). In another embodiment, the pharmaceutical composition comprises 20 nM NaAc. In another embodiment, the pharmaceutical composition comprises 20 mM NaAc and 0.15M NaCl.

In one embodiment, the pharmaceutical composition comprises sodium carbonate ($Na_2CO_3$). In another embodiment, the pharmaceutical composition comprises sodium carbonate ($Na_2CO_3$) in combination with NaCl. In another embodiment, the pharmaceutical composition comprises 50 mM $Na_2CO_3$.

In one embodiment, the pharmaceutical composition comprises dextrose optionally with or without a buffering substance. In another embodiment, the pharmaceutical composition comprises 5% w/w dextrose.

The purine nucleoside or analog thereof can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 millimeters or less in diameter, usually 500 microns ($\mu$m) or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the mean average diameter is less than about 45 $\mu$m, optionally less than 20 $\mu$m, and further between about 0.1 and 10 $\mu$m.

Encapsulation of pharmaceuticals in biocompatible, biodegradable polymer microparticles can prolong the maintenance of therapeutic drug levels relative to administration of the drug itself. Sustained release may be extended up to several months depending on the formulation and the active molecule encapsulated. In order to prolong the existence at the target site, the drug may be formulated within a matrix into a slow release formulation (see, for example, Langer (1998) *Nature*, 392, Supplement, 5-10). Following administration, drug then is released via diffusion out of, or via erosion of the matrix. Encapsulation within biocompatible, biodegradable polyesters, for example, copolymers of lactide and glycolide, has been utilized to deliver small molecule therapeutics ranging from insoluble steroids to small peptides. Presently, there are over a dozen lactide/glycolide polymer formulations in the marketplace, the majority of which are in the form of microparticles (T. Tice, "Delivery with Depot Formulations" *Drug Delivery Technology*, (2004) 4(1)) (http://www.drugdeliverytech.com/cgi-bin/articles.cgi?idArticle=204).

Examples of w/o/w emulsion processes are described in U.S. Pat. Nos. 4,954,298; 5,330,767; 5,851,451 and 5,902,834, each of which are hereby incorporated herein by reference in their entirety. Emulsions may be formed by any suitable method. In one embodiment, a batch device for mixing the first and second phases under turbulent conditions such as with a stirrer as disclosed in U.S. Pat. No. 5,407,609, which is hereby incorporated herein by reference in its entirety. Other batch processes may employ a homogenizer or a sonicator. In another embodiment, an emulsion is formed by continuously mixing the first phase and second phase, in-line, using turbulent flow conditions, as in the use of an in-line dynamic mixer or an in-line static mixer such as described in U.S. Pat. No. 5,654,008, which is hereby incorporated herein by reference in its entirety.

In one embodiment, the microparticles are prepared according to the process disclosed in PCT publication No. WO 2005/003180, which is hereby incorporated by reference in its entirety, which discloses an emulsion-based technique employing a packed bed system that uses laminar flow conditions to produce an emulsion that results in microparticles containing biological or chemical agents after solvent removal.

In another embodiment, the pharmaceutically acceptable formulations comprise lipid-based formulations. Any of the known lipid-based drug delivery systems can be used in the practice of the invention. For instance, multivesicular liposomes (MVL), multilamellar liposomes (also known as multilamellar vesicles or "MLV"). unilamellar liposomes, including small unilamellar liposomes (also known as unilamellar vesicles or "SUV") and large unilamellar liposomes (also known as large unilamellar vesicles or "LUV"), can all be used so long as a sustained release rate of the encapsulated purine nucleoside or analog thereof can be established. In one embodiment, the lipid-based formulation can be a multivesicular liposome system. Methods of making controlled release multivesicular liposome drug delivery systems is described in PCT Application Publication Nos. WO 96/11642, WO 94/12957 and WO 94/04490, the contents of which are incorporated herein by reference in their entirety.

The composition of the synthetic membrane vesicle is usually a combination of phospholipids, usually in combination with steroids, especially cholesterol. Other phospholipids or other lipids may also be used.

Examples of lipids useful in synthetic membrane vesicle production include but are not limited to the following: phosphatidylglycerols, phosphatidylcholines, phosphatidylserines, phosphatidylethanolamines, sphingolipids, cerebrosides, and gangliosides. Preferably phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol are used.

In preparing lipid-based vesicles containing a purine nucleoside or analog thereof, such variables as the efficiency of purine nucleoside encapsulation, lability of the purine nucleoside, homogeneity and size of the resulting population of vesicles, purine nucleoside-to-lipid ratio, permeability, instability of the preparation, and pharmaceutical acceptability of the formulation should be considered (see Szoka, et al., Annual Reviews of Biophysics and Bioengineering, 9:467, 1980; Deamer, et al., in Liposomes, Marcel Dekker, New York, 1983, 27; and Hope, et al., Chem. Phys. Lipids, 40:89, 1986, the contents of which are incorporated herein by reference).

The pharmaceutically acceptable formulations can usefully be suspended in aqueous vehicles and introduced through conventional hypodermic needles or using infusion pumps. Prior to introduction, the formulations can be sterilized with, preferably, gamma radiation or electron beam sterilization, described in U.S. Pat. No. 5,603,972 the contents of which are incorporated herein by reference.

In one embodiment, the pharmaceutical composition is administered in a time-period from about the time of the CNS injury to about 100 hours after the CNS injury. In another embodiment, the pharmaceutical composition is administered within about 24 hours of the CNS injury. In another embodiment, the pharmaceutical composition is administered within about 12 hours of the CNS injury. In another embodiment, the pharmaceutical composition is administered within about 6 hours of the CNS injury.

In one embodiment, the pharmaceutical composition is administered after a delay. In one embodiment, the pharmaceutical composition is administered in a time period ranging from about 1 to 2 weeks after the CNS injury. In another the pharmaceutical composition is administered after about 1 week from the CNS injury. In another the pharmaceutical composition is administered after about 2 weeks from the CNS injury.

For injection, the purine nucleoside formulation of the invention can be formulated in liquid solutions, preferably in physiologically compatible buffers such as Hank's solution or Ringer's solution. In addition, the purine nucleoside formulation may be formulated in solid form and re-dissolved or suspended immediately prior to use. Lyophilized forms are also included. The injection can be, for example, in the form of a bolus injection or continuous infusion (e.g., using infusion pumps) of the purine nucleoside formulation.

Duration and Levels of Administration

In one embodiment of the method of the invention, the pharmaceutically acceptable formulation provides a controlled delivery. In one embodiment the controlled delivery is a sustained delivery. In another embodiment the controlled delivery is a delayed delivery.

In one embodiment of the method of the invention, the pharmaceutically acceptable formulation provides a sustained delivery, e.g., "slow release" of the purine nucleoside to a subject for at least one, two, three, or four weeks after the pharmaceutically acceptable formulation is administered to the subject.

As used herein, the term "sustained delivery" is intended to include continual delivery of a purine nucleoside or analog thereof in vivo over a period of time following administration, preferably at least several days, a week or several weeks. Particular note is made of courses of treatment of about 2 weeks or more, about 4 weeks or more, about 6 weeks or more and as well as chronic administration of about 8 weeks and continuing through manifestation of signs of re-enervation. Sustained delivery of the purine nucleoside or analog thereof can be demonstrated by, for example, the continued therapeutic effect of the purine nucleoside or analog thereof over time (e.g., sustained delivery of the purine nucleoside or analog thereof can be demonstrated by continued outgrowth or by continued inhibition of outgrowth of CNS neurons over time). Alternatively, sustained delivery of the purine nucleoside or analog thereof may be demonstrated by detecting the presence of the purine nucleoside or analog thereof in vivo over time.

In one embodiment, the pharmaceutically acceptable formulation provides sustained delivery of the purine nucleoside or analog thereof to a subject for less than 30 days after the purine nucleoside or analog thereof is administered to the subject. For example, the pharmaceutically acceptable formulation, e.g., "slow release" formulation, can provide sustained delivery of the purine nucleoside or analog thereof to a subject for one, two, three or four weeks after the purine nucleoside or analog thereof is administered to the subject. Alternatively, the pharmaceutically acceptable formulation may provide sustained delivery of the purine nucleoside or analog thereof to a subject for more than 30 days after the purine nucleoside or analog thereof is administered to the subject.

In one embodiment, the purine nucleoside or analog thereof is administered by intravenous infusion for 1 week. In another embodiment, the purine nucleoside or analog thereof is administered by intravenous infusion for 2 weeks. In another embodiment, the purine nucleoside or analog thereof is administered by intravenous infusion for 3 weeks. In another embodiment, the purine nucleoside or analog thereof is administered by intravenous infusion for about 4 weeks or more.

The pharmaceutical formulation, used in the method of the invention, contains a therapeutically effective amount of the purine nucleoside or analog thereof. A "therapeutically effective amount" refers to an amount effective, at dosages and for periods of time necessary, to achieve the desired result. A therapeutically effective amount of the purine nucleoside or analog thereof may vary according to factors such as the disease state, age, and weight of the subject, and the ability of the purine nucleoside or analog thereof (alone or in combination with one or more other agents) to elicit a desired response in the subject. Dosage regimens may be adjusted to provide the optimum therapeutic response. A therapeutically effective amount is also one in which any toxic or detrimental effects of the purine nucleoside or analog thereof are outweighed by the therapeutically beneficial effects.

In one embodiment, a non-limiting range for a therapeutically effective concentration is about 1 nM to 1 M. In another embodiment, a range for a therapeutically effective concentration is about 1 µM to 100 mM. In another embodiment, the therapeutically effective concentration is about 1 mM to 100 mM. In another embodiment, the therapeutically effective concentration is about 1 mM to 75 mM.

In one embodiment, the therapeutically effective concentration of inosine is about 10 mM. In another embodiment, the therapeutically effective concentration of inosine is about 50 mM. In another embodiment, the therapeutically effective concentration of inosine is about 75 mM. In another embodiment, the therapeutically effective concentration of inosine is about 100 mM. In another embodiment, the therapeutically effective concentration of inosine is about 500 mM.

In one embodiment, a non-limiting range for an administered dose concentration is about 1 nM to 1 M. In another embodiment, the administered dose concentration is about 1 µM to 100 mM. In another embodiment, the administered dose concentration is about 1 mM to 100 mM. In another embodiment, the administered dose concentration is about 1 mM to 75 mM.

In one embodiment, the administered dose concentration of inosine is about 10 mM. In another embodiment, the administered dose concentration of inosine is about 50 mM. In another embodiment, the administered dose concentration of inosine is about 75 mM. In another embodiment, the administered dose concentration of inosine is about 100 mM. In another embodiment, the administered dose concentration of inosine is about 500 mM.

Generally, the compositions of this invention are dispensed in unit dosage form comprising about 0.1 mg to 100 g in a pharmaceutically acceptable carrier per unit dosage. In one embodiment, inosine is administered using a dose of about 0.1 mg/kg/day to 100 g/kg/day. In another embodiment, inosine is administered using a dose of about 1 g/kg/day to 10 g/kg/day. In another embodiment, inosine is administered using a dose of about 1 g/kg/day. In another embodiment, inosine is administered using a dose of about 5 g/kg/day. In another embodiment, inosine is administered using a dose of about 10 g/kg/day.

In one embodiment, a non-limiting regimen of purine nucleoside or analog thereof provides a steady state extracellular fluid concentration of about 0.1 µM to 10 mM. In another embodiment the pharmaceutical provides a steady state extracellular fluid concentration of about 1 µM to 0.1 mM. In another embodiment the pharmaceutical provides a steady state extracellular fluid concentration of about 1 µM. In another embodiment the pharmaceutical provides a steady state extracellular fluid concentration of about 10 µM. In another embodiment the pharmaceutical provides a steady state extracellular fluid concentration of about 100 µM. In another embodiment the pharmaceutical provides a steady state extracellular fluid concentration of about 1 mM. In another embodiment the pharmaceutical provides a steady state extracellular fluid concentration of about 10 mM. In another embodiment the pharmaceutical provides a steady state extracellular fluid concentration of about 100 mM.

It is to be noted that dosage values may vary with the severity of the condition to be alleviated. It is to be further understood that for any particular subject, specific dosage regimens should be adjusted over time according to the individual need and the professional judgment of the person administering or supervising the administration of the purine nucleoside or analog thereof and that dosage ranges set forth herein are exemplary only and are not intended to limit the scope or practice of the claimed invention.

The invention, in another embodiment, provides a pharmaceutical composition consisting essentially of a purine nucleoside or analog thereof and a pharmaceutically acceptable carrier and methods of use thereof to modulate axonal outgrowth by contacting CNS neurons with the composition via internalized administration. In one embodiment, the term "consisting essentially of" is meant that the pharmaceutical composition does not contain any other modulators of neuronal growth such as, for example, nerve growth factor (NGF). In one embodiment, the pharmaceutical composition of the invention can be provided as a packaged formulation. The packaged formulation may include a pharmaceutical composition of the invention in a container and printed instructions for administration of the composition for treating a subject having a disorder associated with an injury of central nervous system neurons, e.g., an injury to retinal ganglion cells, a spinal cord injury or a traumatic brain injury.

For internalized administration, attention is drawn to injectable, sterile solutions, including both oily and aqueous solutions, as well as suspensions, emulsions, or implants. Ampules are convenient unit dosages.

Sustained or directed release compositions can be formulated, e.g., liposomes or those wherein the inosine or other purine is protected with differentially degradable coatings, e.g., by microencapsulation, multiple coatings, etc. It is also possible to freeze-dry the new compositions and use the lyophilizates obtained, for example, for the preparation of products for injection.

In one embodiment the dosage, when administered to patients including, but not limited to, humans, to treat CNS trauma or insult, is analogous to the known intrathecal dose of inosine (particularly if the general dosage range spans an order of magnitude or more).

The compounds of this invention can be formulated with pharmaceutically acceptable carriers into unit dosage forms in a conventional manner so that the patient in need of therapy can periodically (e.g., once or more per day) take a compound according to the methods of this invention. The exact initial dose of the compounds of this invention can be determined with reasonable experimentation. The initial dosage calculation would also take into consideration several factors, such as the formulation and mode of administration of the particular compound.

It will be appreciated that the actual preferred amounts of active compositions in a specific case will vary according to the specific compositions being utilized, the particular compositions formulated, the mode of administration, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

The compounds of the present invention may also be combined with one or more additional agents having utility in modulating the axonal outgrowth of central nervous system neurons.

In one embodiment, the compounds of the present invention are administered in combination with a macrophage derived factor or neurotrophic factor such as oncomodulin or TGF-β (see U.S. Pat. No. 6,855,690 and U.S. Patent Application Publication Nos. 2005/0054558 and 2005/059594, the contents of each are incorporated herein by reference in their entirety). In one embodiment, the compounds of the present invention are administered in combination with one or more modulators of intracellular signal transduction.

In one embodiment, the compounds of the present invention are administered in combination with one or more modulators of molecular targets that promote axon regeneration. In one embodiment, the molecular target is a kinase or a receptor kinase. In one embodiment, the molecular target is an antiregenerative factor or a receptor for an antiregenerative factor In one embodiment, the compounds of the present invention are administered in combination with one or more modulators of an antiregenerative factor. In another embodiment, the compounds of the present invention are administered in combination with one or more modulators of a receptor for an antiregenerative factor. In another embodiment, the compounds of the present invention are administered in combination with one or more inhibitors of antiregenerative factors. In another embodiment, the compounds of the present invention are administered in combination with one or more inhibitors of a receptor for an antiregenerative factor.

Examples of kinases include, but are not limited to, receptor linked kinases such as EGFR, and intracellular kinases such as JNK, ROCK and RhoA. Thus, inhibitors of such kinases, e.g., cethrin, are indicated as adjuncts to inosine therapy.

Examples of antiregenerative factor receptors include, but are not limited to, EGFR, and Nogo receptor complexes comprising Lingo, TROY and p75.

Examples of EGFR inhibitors include, but are not limited to, Tarceva® (erlotinib, OSI Pharmaceuticals, Farmingdale, N.Y.) and Iressa® (gefitinib, AstraZeneca London, UK), mannose, AG1478, PD168393, GW2016, GW572016, PK1166, CL-1033, CI-1033, EKB-569 and GW2016 cetuximab, panitumumab, TheraCIM, EMD 72000 and MDX447 (see U.S. patent application Ser. No. 11/180,070, which is incorporated herein by reference in its entirety).

Examples of JNK inhibitors include, but are not limited to, JNK3 inhibitors, JSP1 inhibitor, CEP-1347, BF-67192, AS-602801, XG-101, AM-111, JNK-401, JNK-930, JNK-9359, CEP-11004, PMI-002, XG-102 and those described in U.S. Pat. Pub No. 2006/0122179, U.S. Pat No 6,987,184 to Sakata et al; U.S. Pat. No. 7,084,159 to Cao et al; U.S. Pat Publ No. 20050148624 to Itoh et al; and Kuan and Burke, *Curr Drug Targets CNS Neurol Disord* (2005) 4:63-7). Exemplary JNK pathway inhibitors include CEP-1347 (Maroney et al, *J Neurosci*. (1998) 18:104-11), SP600125 (Bennett et al, *Proc Natl Acad Sci U S A*. (2001) 98:13681-6), AS601245 (Carboni et al, *J Pharmacol Exp Ther*. (2004) 310:25-32), DJNK1 (Manning and Davis, Nat Rev Drug Discov. (2003) 2:554-65), AS-602801 (Halazy, ARKIVOC (2006) vii:496-508), XG-102 (Borsello et al, *Nat Med*. (2003) 9:1180-6.), AM-111 (Coleman et al, *Hear Res*. (2006) July 14; [Epub ahead of print]), CC-401 (Uehara et al, *J Hepatol*. (2005) 42:850-9), and CEP-11004 (Ganguly et al, *J Neurochem*. January 2004; 88 (2):469-80). In one embodiment, the inhibitor is siRNA targeted to a JNK pathway member (e.g. JNK1, JNK2, and JNK3). Each of the above references are incorporated by reference in their entirety.

In one embodiment, the purine nucleoside or analog thereof is co-administered with an application of an electrical stimulus such as oscillating field stimulation (OFS) OFS may be applied using an Andara™ OFS PLUS System, Cyberkinetics Neurotechnology Systems, Inc. Foxborough, Mass. (see U.S. Patent Application Publication No. 2004/0214790, which is incorporated herein by reference in its entirety).

In one embodiment, compounds of the present invention are administered in combination with an agent that facilitates transport of drugs across the blood brain barrier and into the central nervous system (CNS). Examples of such transport agent include, but are not limited to, Lipobridge® (Genzyme Pharmaceuticals, Cambridge, Mass.), a short chain oligoglycerolipid.

Compositions for intravenous administration optionally comprise sterile isotonic aqueous buffer. Optionally, the compositions include a solubilizing agent. Compositions for intravenous administration optionally include a local anesthetic such as lidocaine and/or prilocaine.

Ingredients may be supplied either separately or mixed together in unit dosage form. In one embodiment, the ingredients are supplied as a dry lyophilized powder or water-free concentrate in a hermetically sealed container such as an ampule indicating the quantity of active agent. Where the purines are to be administered by infusion, they can be dispensed, for example, with an infusion bottle containing sterile pharmaceutical grade water or saline. Where the purines are administered by injection, an ampule of sterile water for injection or saline can be provided so that the ingredients can be mixed prior to administration.

The dosage of each formulation depends on several factors including the severity of the condition, and the age, weight, and health of the subject to be treated. Additionally, pharmacogenomic (the effect of genotype on the pharmacokinetic, pharmacodynamic or efficacy profile of a therapeutic) information about a particular patient may affect dosage used. Furthermore, one skilled in the art will appreciate that the exact individual dosages may be adjusted somewhat depending on a variety of factors, including the specific composition being administered, the time of administration, the route of administration, the nature of the formulation, the rate of excretion, the particular disorder being treated, the severity of the disorder, and the anatomical location of the disorder. Wide variations in the needed dosage are to be expected in view of the differing efficiencies of the various routes of administration. Variations in these dosage levels can be adjusted using standard empirical routines for optimization, which are well-known in the art. The precise therapeutically effective dosage levels and patterns are typically determined by the attending physician in consideration of the above-identified factors.

The invention optionally relates to combining separate pharmaceutical compositions in a pharmaceutical pack. The combination of the invention is therefore optionally provided as components of a pharmaceutical pack. The components can be formulated together or separately and in individual dosage amounts.

It will be understood that the compositions of the invention optionally include corresponding salts, analogs, derivatives, prodrugs, stereoisomers, and polymorphs thereof.

EXAMPLES

The following examples serve to illustrate certain useful embodiments and aspects of the present invention and are not to be construed as limiting the scope thereof.

Example 1

Evaluation of Effectiveness on Central Nervous System Neurons

Modulation of CNS neurons is evaluated by any accepted method of measuring axon regeneration. This includes direct observation and indirect evaluation such as by evaluating subjective symptoms or objective physiological indicators. Treatment efficacy, for example, may be evaluated based on a neurological examination, electrophysical examination, intact segmental reflex examination or any combination thereof. (see Borgens et al. *Restor. Neurol. Neurosci*. 1993, 5, 305-322, which is incorporated herein by reference in its entirety).

Treatment efficacy for evaluating subjects may also be defined in terms of stabilizing or improving neurological, electrophysical and reflex properties. In determining the effectiveness of a particular therapy in treating CNS disorders, patients may also be clinically evaluated by a practitioner several days after administration and/or at least one-month later.

Example 2

In Vivo Evaluation of Cortical Rewiring after Brain Injury

Modulation of CNS neurons is evaluated by any accepted method of measuring axon regeneration. (See N. Dancause et al. 2005, *J. Neurosci*. 25(44) 10167-10179, which is incorporated herein by reference in its entirety.) A model for post stroke motor recovery and focal cerebral ischemia uses non-human primates such as squirrel monkey, baboon and macaque (see, S. Fukuda et al., *ILAR Journal* 2003, 44(2) 96-104, which is incorporated herein by reference in its entirety). A squirrel monkey model is used to assess post-stroke motor recovery (see R. J. Nudo et al., *ILAR Journal* 2003, 44(2) 161-174, which is incorporated herein by reference in its entirety).

Example 3

Determination of the Relationship between Infusion Time and Inosine Concentration in the Extracellular Fluid of the Brain A cohort of 4 to 12 patients (each patient implanted with a microdialysis catheter to manage elevated intracranial pressure in an intensive care setting) receives IV inosine at a constant infusion rate for 2 hours. Before, during and after the infusion, samples of brain extracellular fluid are obtained from the catheter at 30 to 60 minute intervals. The samples are used to determine the relationship between infusion time and inosine concentration in the extracellular fluid of the brain. In additional cohorts, increased infusion rates are studied in a similar fashion to determine the relationship between infusion rate, infusion time and inosine concentration in the extracellular fluid of the brain.

Example 4

Determination of Treatment Regimen of Inosine for Stroke

A) Four groups of 50 to 500 subjects, each with onset of stoke within 12 hours of their random allocation and assignment to a treatment group, receive an intravenous infusion of vehicle (placebo) or one of 3 doses (or infusion rates) of inosine for 1 to 2 weeks. Using any or several neurological rating scales, each patient's condition before treatment begins, and for at least 90 days after the onset of symptoms, are measured. The outcome for each treatment group is compared to the vehicle treatment to determine the safe and effective treatment regimen for inosine.
B) Four groups of 50 to 500 subjects, each with onset of stoke within 1 week of their random allocation and assignment to a treatment group, receive an intravenous infusion of vehicle (placebo) or one of 3 doses (or infusion rates) of inosine for 1 to 2 weeks. Using any or several neurological rating scales, each patient's condition before treatment begins, and for at least 90 days after the onset of symptoms, is measured. The outcome for each treatment group is compared to the vehicle treatment to determine the safe and effective treatment regimen for inosine.

Example 5

Intravenous Formulation of Inosine

A subject with central nervous system injury, is treated with an intravenous infusion of a solution of inosine (50 mM) and NaCl (0.15M) at a rate of 1 g/kg/day. Amelioration of the neurological deficit is noted.

Example 6

Intravenous Formulation of Inosine

A subject with an onset of stroke, is treated with an intravenous infusion of a solution of inosine (50 mM) and NaCl (0.15M) at a rate of 1 g/kg/day. Amelioration of the neurological deficit is noted.

Example 7

Intravenous Formulation of Inosine

A subject with a spinal cord injury, is treated with an intravenous infusion of a solution of inosine (50 mM) and NaCl (0.15M) at a rate of 1 g/kg/day. Amelioration of the neurological deficit is noted.

Example 8

Intravenous Formulation of Inosine

A subject with a traumatic brain injury, is treated with an intravenous infusion of a solution of inosine (50 mM) and NaCl (0.15M) at a rate of 1 g/kg/day. Amelioration of the neurological deficit is noted.

Example 9

Subcutaneous Formulation of Inosine

A subject with central nervous system injury, is treated with a subcutaneous injection of a solution of inosine (50 mM) and NaCl (0.15M) at a rate of 1 g/kg/day. Amelioration of the neurological deficit is noted.

Example 10

Subcutaneous Formulation of Inosine

A subject with an onset of stroke, is treated with an subcutaneous injection of a solution of inosine (50 mM) and NaCl (0.15M) at a rate of 1 g/kg/day. Amelioration of the neurological deficit is noted.

Example 11

Subcutaneous Formulation of Inosine

A subject with a spinal cord injury, is treated with an subcutaneous injection of a solution of inosine (50 mM) and NaCl (0.15M) at a rate of 1 g/kg/day. Amelioration of the neurological deficit is noted.

Example 12

Subcutaneous Formulation of Inosine

A subject with a traumatic brain injury, is treated with subcutaneous injection of a solution of inosine (50 mM) and NaCl (0.15M) at a rate of 1 g/kg/day. Amelioration of the neurological deficit is noted.

Example 13

Intravenous Formulation of Inosine

A subject with central nervous system injury is treated with intravenous infusion of a solution of inosine in a formulation of 0.1% sodium bicarbonate 70 mg/mL inosine, pH9.2. The 250 ml of the inosine formulation is infused over a two hour period. This procedure is repeated for 14 days. Amelioration of the neurological deficit is noted.

Dosages of inosine from about 5 to about 25 mg per day are noted. Presuming an intravenous infusion of about 250 ml over about 2 hours, a dosage of about 10 to 20 gm results.

Particular mention is made of dosages in the 10-20 gm range. Daily dosages for one, two or more weeks are noted. Such dosages are also expressed as about 0.15 to about 0.3 g/kg/day. Daily dosages from about 0.015 to about 3 g/kg/day are contemplated.

Example 14

Two groups of three rats were dosed intravenously with a total of 4 different concentrations of inosine and vehicle, providing within-subjects comparisons. Rats were anesthetized and each was surgically implanted above the medial prefrontal cortex (A-P +3.2 and M-L +1.0 from Bregma, D-V −2.0 from the skull surface) with an intracerebral guide cannula that was replaced after three days by a microdialysis probe. The microdialyses probes were continually flushed with artificial cerebrospinal fluid (aCSF). Catheters were inserted into the jugular vein for inosine dosing and into the femoral artery for blood collection.

Inosine formulated in aqueous bicarbonate buffer (pH 9.2) was administered by intravenous infusion for up to two hours to two groups of rats (N=3 per group) and the microdialysis probes were perfused with aCSF at a rate of 0.015 mL/minute. One group received nominal dose rates of 0 (vehicle), 100, and 300 mg/kg/hour, and the other group received nominal dose rates of 0, 500, and 700 mg/kg/hour. Each nominal infusion rate was 10 mL/kg/hour and was separated by a 2-day washout period.

Blood samples and brain microdialysates were collected prior to each dose to establish basal concentrations of inosine, and for a period of 2 hrs after each dose to determine the percent of change (increase, decrease, or none) relative to basal. Microdialysate and blood plasma inosine concentrations were measured using an LC/MS/MS assay. The lower limit of quantitation of the rat plasma analysis and the CNS microdialysate was 0.25 ng/mL.

The subjects were naïve, male, Sprague-Dawley rats procured for this study from Harlan Spraque Dawley, Inc. (Indianapolis, Ind.). All rats selected for surgeries were quarantined, inspected and deemed acceptable for surgery by technicians qualified to make this assessment. Intracerebral guide cannulae were surgically implanted above the medial prefrontal cortex (mPFC). Rats were provided with a single dose of analgesic immediately after surgery to alleviate discomfort. Animals were inspected frequently during post-surgical recovery. After 3 days, the stylet in the intracerebral guide cannula was replaced with a microdialysis probe.

All study subjects were dosed via JVC catheters without handling. Prior to collecting pre-dose microdialysates, glass vials were loaded with the appropriate drug solution and connected to an Empis system. All rats received the doses of inosine they were intended to receive, as the infusion rate was ~50 µl/min over the 2 hr dosing period. Two days later, all rats received the doses of inosine they were intended to receive, as the infusion rate was ~50 µl/min over the 2 hr dosing period. All rats then received reduced doses of inosine, as the infusion rat was reduced to ~40 µl/min over a 2 hr dosing period.

Samples of CNS microdialysate (0.03 mL) and arterial blood (0.15 mL) were taken for analysis of inosine concentration before infusion, and at specified times after the start of the infusions (20, 40, 60, 80, and 120 minutes).

Solutions:
0.1M $NaHCO_3$ solution (vehicle):
1) Dispense 100 mg of $NaHCO_3$
2) Add nanopure $H_2O$.
3) Adjust pH to 9.2
4) QS to 100 mL with nanopure $H_2O$
5) Filter with 0.2 µm sterile syringe filter
10 mg/mL inosine solution:
1) Dispense 0.4 g of inosine
2) Dispense 40 mg of $NaHCO_3$
2) Add nanopure $H_2O$.
3) Adjust pH to 9.2
4) QS to 40 mL with nanopure $H_2O$
5) Filter with 0.2 µm sterile syringe filter
30 mg/mL inosine solution:
1) Dispense 1.2 g of inosine
2) Dispense 40 mg of $NaHCO_3$
2) Add nanopure $H_2O$.
3) Adjust pH to 9.2
4) QS to 40 mL with nanopure $H_2O$
5) Filter with 0.2 µm sterile syringe filter
50 mg/mL inosine solution:
1) Dispense 2.0 g of inosine
2) Dispense 40 mg of $NaHCO_3$
2) Add nanopure $H_2O$.
3) Adjust pH to 9.2
4) QS to 40 mL with nanopure $H_2O$
5) Filter with 0.2 µm sterile syringe filter
70 mg/mL inosine solution:
1) Dispense 2.8 g of inosine
2) Dispense 40 mg of $NaHCO_3$
2) Add nanopure $H_2O$.
3) Adjust pH to 9.2
4) QS to 40 mL with nanopure $H_2O$
5) Filter with 0.2 µm sterile syringe filter
Composition of Artificial Cerebrospinal Fluid (aCSF):
NaCl 145 mM, KCl 2.8 mM, $MgCl_2$ 1.2 mM, $CaCl_2$ 1.2 mM, and D-Glucose 5.4 mM.
Extracellular Concentration (Dialysate):
Changes in inosine concentrations are expressed as percent of baseline in order to compare changes in inosine concentrations between treatments.
Percent of Baseline:
Changes in inosine concentrations (percent of baseline) were determined by dividing a particular post-dose inosine concentration (ng/mL) by the average of 4 pre-dose (baseline) inosine concentrations (ng/mL) and multiplying this value by 100%. Where plasma inosine (µg/mL) values appeared to reach steady-state by inspection of the last three time points, approximately values for clearance (L/kg/hour) were obtained from the relationship, clearance=infusion rate (mg/kg/hour)/steady-state concentration (mg/L). Mean percent of baseline changes in inosine concentrations were plotted for each treatment condition. The data suggest that intravenous dosages of inosine are effective in terms of increasing the concentrations of inosine in the mPFC of the rat.

Table 2 presents a 5 day intravenous inosine microdialysis protocol for use in conscious rats. The dose regimens for the three rats in each of the two groups are indicated.

Example 15

This example considers intravenous infusion of inosine in rodent model of acute spinal cord injury. Rats were anesthetized and each was subjected to laminectomy in the thoracic region of the spinal cord, followed by dorsal hemisection of the spinal cord that included severance of the cortical spinal tract as a model of spinal cord injury (SCI). These rats were divided into two groups: one group was dosed by continuous intravenous infusion of 70 mg/mL (261 mM) inosine formulated in 0.1% sodium bicarbonate solution, pH approximately 9.2, for four weeks, and the other group was dosed by continuous intravenous infusion with 0.1% sodium bicarbonate vehicle control for four weeks. The infusion rate was 10 microliters per hour for inosine (approximately 2 mg/kg/hr) and vehicle dosing, and the infusions were started immediately after the SCI. In this regard it is noted that dosing at 2 mg/kg/hr represents a dose of about 48 mg/kg/day. In a 70 kg subject this is equivalent to about 3-4 g/day. Attention is drawn to daily doses from about 1 g/day to about 10 gm/day with attention being drawn to doses of about 2 g/day and about 5 day.

Rats were evaluated one day post-SCI to verify completeness of the lesion, and then weekly for functional status by assessment using the Basso-Beattie-Bresnahan (BBB) score of locomotor function as judged by hind-limb function and forelimb:hind-limb coordination. The maximal score possible is 21, which represents complete recovery of motor function, and the minimal score is zero, which represents complete limb paralysis.

Rats had BBB scores of motor function that were near zero immediately after injury, verifying the completeness of the lesion. Rats that received an intravenous inosine infusion showed continual or sustained improvement in their functional outcome over the four weeks of the study, as assessed by the their BBB scores, which were near maximal possible values at three to four weeks post-SCI, indicating a nearly complete recovery. In contrast, rats that received only vehicle infusion did not fully recover motor function at four weeks and their BBB scores were less than half those of the inosine treated rats. The differences in BBB scores between inosine-treated rats and vehicle-treated rats were statistically significant at weeks one and two ($P<0.01$), and weeks three and four ($P<0.001$) (FIG. 3).

Figure 3A:
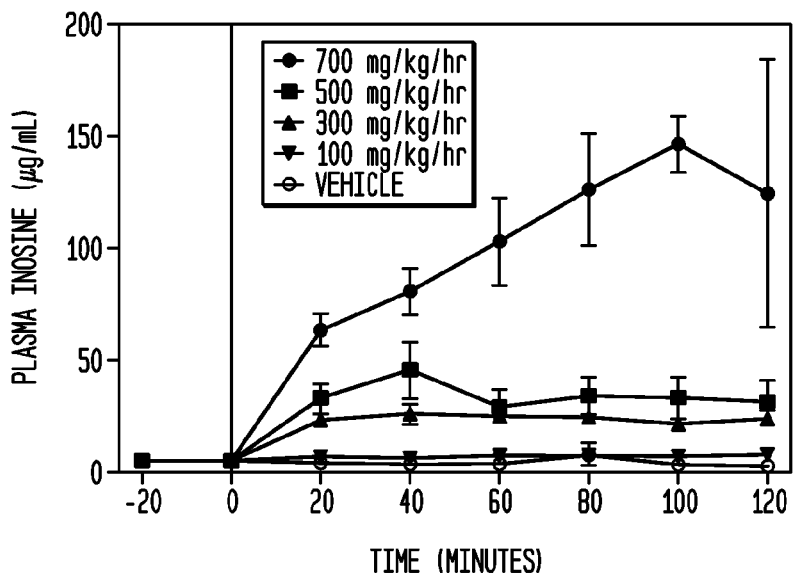
FIG. 3A presents plasma inosine in µg/mL.
Figure 3B:
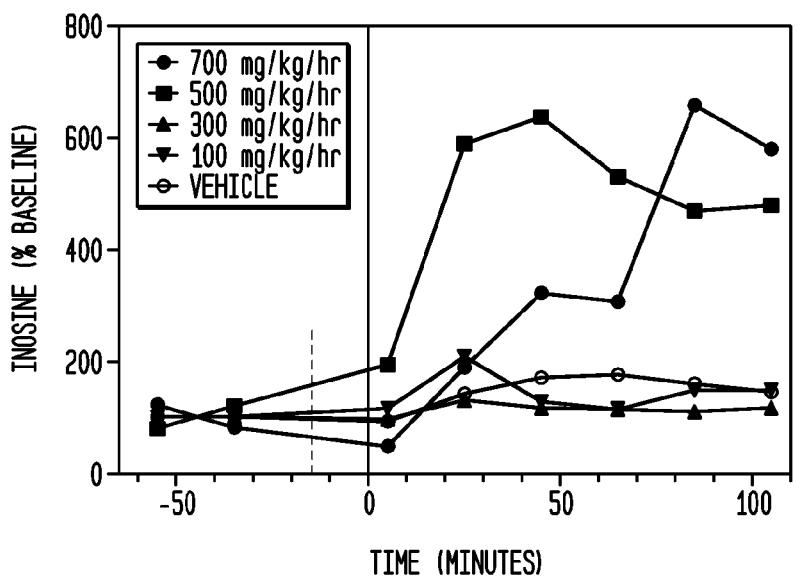
FIG. 3B presents microdialysate inosine in %/baseline.
Figure 4:
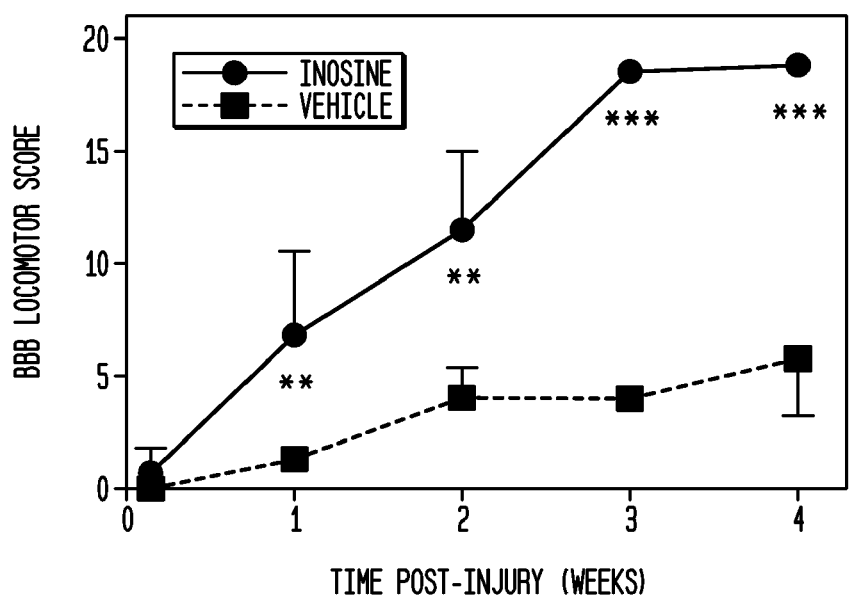
FIG. 4. presents data on inosine dosed by continuous intravenous infusion. As can be see, dosing improves functional outcome in a rat hemisection model of spinal cord injury. P<0.01; *P<0.001 vs. vehicle infusion.

FIG. 1 and FIG. 2 and FIG. 3 present the analysis of the plasma and microdialysate levels of inosine in the group one and group two rats, repectively. Plasma inosine concentrations were dose-dependently increased with maximal values up to 5.0, 7.2, 26, 45, and 146 µg/mL at inosine dose rates of 0, 100, 300, 500 and 700 mg/kg/hr, respectively. Steady-state mean plasma inosine levels appeared to be reached during infusion rates of 300 mg/kg/hour (22.8 µg/mL) and 500 mg/kg/hour (32.4 µg/mL), allowing values for clearance of 13.1 and 15.4 L/kg/hour, respectively, to be calculated. Basal CNS microdialysate inosine concentrations were highly variable (0.138-1.40 ng/mL) over different sampling days within and between animals, and were therefore expressed as percent of the mean of two baseline values taken within 40 minutes before each infusion. No differences in CNS microdialysate inosine percent increases were reliably seen between inosine dose rates of 0 (90-175%), 100 (113-146%), and 300 (96-116%) mg/kg/hour. However, maximal increases of 526-632% and 574-653% were seen within 45 minutes after inosine dose rates of 500 and 700 mg/kg/hour, respectively, and % increases remained well above baseline for the remainder of these infusions.

Incorporation by Reference

The patent and scientific literature referred to herein establishes knowledge that is available to those of skill in the art. All issued patents, patent applications, published foreign applications, and published references that are cited herein, are hereby incorporated by reference to the same extent as if each was specifically and individually indicated to be incorporated by reference in their entirety.

Equivalents

Those skilled in the art will recognize, or be able to ascertain, using no more than routine experimentation, numerous equivalents to the specific embodiments described specifically herein. Such equivalents are intended to be encompassed in the scope of the following claims.

TABLE 2

| | Day 1 2-hr Infusion | | Day 3 2-hr Infusion | | Day 5 2-hr Infusion |
|---|---|---|---|---|---|
| | Group One | | | | |
| Rat #1 | 0 mg/kg/hr | 48-hr Washout | 100 mg/kg/hr | 48-hr Washout | 300 mg/kg/hr |
| Rat #2 | 100 mg/kg/hr | 48-hr Washout | 300 mg/kg/hr | 48-hr Washout | 0 mg/kg/hr |
| Rat #3 | 300 mg/kg/hr | 48-hr Washout | 0 mg/kg/hr | 48-hr Washout | 100 mg/kg/hr |
| | Group Two | | | | |
| Rat #4 | 0 mg/kg/hr | 48-hr Washout | 500 mg/kg/hr | 48-hr Washout | 700 mg/kg/hr |
| Rat #5 | 500 mg/kg/hr | 48-hr Washout | 700 mg/kg/hr | 48-hr Washout | 0 mg/kg/hr |
| Rat #6 | 700 mg/kg/hr | 48-hr Washout | 0 mg/kg/hr | 48-hr Washout | 500 mg/kg/hr |

We claim:

1. A method for stimulating the axonal outgrowth of central nervous system neurons following central nervous system injury in a mammal in need thereof, comprising administration of a pharmaceutical composition comprising an effective amount of inosine such that axonal outgrowth is stimulated in vivo,
further comprising co-administration of a therapeutically effective dosage of an inhibitor of a kinase selected from the group consisting of c-Jun N-terminal kinase (JNK), Rho-associated protein kinase (ROCK) and Ras homolog gene family, member A (RhoA).

2. A method for stimulating the axonal outgrowth of central nervous system neurons following central nervous system injury in a mammal in need thereof, comprising administration of a pharmaceutical composition comprising an effective amount of inosine such that axonal outgrowth is stimulated in vivo,
further comprising co-administration of a therapeutically effective dosage of BA-210 C3 exoenzyme fibrin sealant mixture (Cethrin®).

* * * * *